US010588715B2

(12) United States Patent
Anderson et al.

(10) Patent No.: US 10,588,715 B2
(45) Date of Patent: Mar. 17, 2020

(54) SYSTEM AND METHOD FOR TREATING SLEEP APNEA WHILE STRAIGHTENING TEETH

(71) Applicants: Margaret Anderson, Rockford, IL (US); FRANTZ DESIGN INCORPORATED, Austin, TX (US)

(72) Inventors: Margaret M. Anderson, Rockford, IL (US); Donald Frantz, Katy, TX (US); Joseph Frantz, Austin, TX (US)

(73) Assignee: Frantz Design Inc., Austin, TX (US)

( * ) Notice: Subject to any disclaimer, the term of this patent is extended or adjusted under 35 U.S.C. 154(b) by 0 days.

(21) Appl. No.: 16/075,595

(22) PCT Filed: Feb. 2, 2017

(86) PCT No.: PCT/US2017/016182
§ 371 (c)(1),
(2) Date: Aug. 4, 2018

(87) PCT Pub. No.: WO2017/136530
PCT Pub. Date: Aug. 10, 2017

(65) Prior Publication Data
US 2019/0262100 A1     Aug. 29, 2019

Related U.S. Application Data

(60) Provisional application No. 62/292,249, filed on Feb. 6, 2016.

(51) Int. Cl.
*A61C 3/00* (2006.01)
*A61C 7/00* (2006.01)
(Continued)

(52) U.S. Cl.
CPC ............... *A61C 7/002* (2013.01); *A61B 1/24* (2013.01); *A61C 7/08* (2013.01); *A61C 7/36* (2013.01); *A61C 13/0019* (2013.01); *A61F 5/566* (2013.01)

(58) Field of Classification Search
CPC ....... A61C 7/002; A61C 7/08; A61C 13/0019; A61C 7/36; A61B 1/24; A61F 5/566
See application file for complete search history.

(56) References Cited

U.S. PATENT DOCUMENTS

| 6,109,265 A | 8/2000 | Frantz et al. |
| 2009/0036889 A1 | 2/2009 | Callender |

(Continued)

FOREIGN PATENT DOCUMENTS

| JP | 2010540087 | 12/2010 |
| JP | 2013523272 | 6/2013 |

(Continued)

OTHER PUBLICATIONS

Written Opinion of IPEA PCT/US2017/016182 dated Feb. 13, 2018.
PCT International Preliminary Report on Patentability PCT/US17/16182 dated Jun. 4, 2018.

*Primary Examiner* — Nicholas D Lucchesi
(74) *Attorney, Agent, or Firm* — Margaret Anderson (57) ABSTRACT

A computationally implemented method includes, but is not limited to: determining an incrementally progressive series of adjustment appliances, each of the series of adjustment appliances having geometries selected to progressively reposition teeth; and determining for each of the series of adjustment appliances, a vertical displacement and a forward mandibular position for treating sleep apnea. In addition to the foregoing, other method aspects are described in the claims, drawings, and text forming a part of the present disclosure.

20 Claims, 6 Drawing Sheets

(51) Int. Cl.
    *A61B 1/24*    (2006.01)
    *A61C 7/08*    (2006.01)
    *A61C 7/36*    (2006.01)
    *A61C 13/00*   (2006.01)
    *A61F 5/56*    (2006.01)

(56)          References Cited

U.S. PATENT DOCUMENTS

2010/0219546 A1    9/2010   Puttler
2013/0122448 A1    5/2013   Kitching
2015/0007830 A1    1/2015   Remmers
2015/0013688 A1*   1/2015   Frantz .................... B29C 51/14
                                                         128/848
2015/0238280 A1    8/2015   Wu et al.
2015/0238284 A1    8/2015   Wu
2015/0342545 A1*  12/2015   Bergersen ................ A61B 6/14
                                                          378/62
2015/0374536 A1*  12/2015   Wagner .................. A61C 7/006
                                                         128/848
2017/0224441 A1*   8/2017   Anderson ................ A61B 1/24

FOREIGN PATENT DOCUMENTS

WO       2011126854       10/2011
WO       2012172112       12/2012
WO       2015149127       10/2015
WO       2016004415        1/2016
WO       2016100577        6/2016

* cited by examiner

SYSTEM AND METHOD FOR TREATING SLEEP APNEA WHILE STRAIGHTENING TEETH

CROSS-REFERENCE TO RELATED APPLICATIONS

This application is a National Stage Patent Application under 35 U.S.C. 371 of International Application no. PCT/US2017/016182, entitled "SYSTEM AND METHOD FOR TREATING SLEEP APNEA WHILE STRAIGHTENING TEETH", filed Feb. 2, 2017, which claims benefit under 35 U.S.C. § 119(e) from U.S. Provisional Patent Application No. 62/292,249, entitled "SYSTEM AND METHOD FOR TREATING SLEEP APNEA WHILE STRAIGHTENING TEETH", filed Feb. 6, 2016, all of which are hereby incorporated herein by reference in its entirety.

FIELD OF INVENTION

This invention relates generally to the field of dental appliances and methods for using dental appliances for treating sleep apnea while straightening teeth.

SUMMARY

A method includes, but is not limited to determining an incrementally progressive series of adjustment appliances, each of the series of adjustment appliances having geometries selected to progressively reposition teeth; and determining for each of the series of adjustment appliances, a vertical displacement and a forward mandibular position for treating sleep apnea. In addition to the foregoing, other method aspects are described in the claims, drawings, and text forming a part of the present disclosure.

In one or more various aspects, related systems include hut are not limited to circuitry and/or programming for effecting the herein-referenced method aspects; the circuitry and/or programming can be virtually any combination of hardware, software, and/or firmware in one of more machines or article of manufacture configured to effect the herein-referenced method aspects depending upon the design chokes of the system designer.

A dental system includes, but is not limited to: means for determining an incrementally progressive series of adjustment appliances, each of the series of adjustment appliances having geometries selected to progressively reposition teeth; and means for determining for each of the series of adjustment appliances, a vertical displacement and a forward mandibular position for treating sleep apnea. In addition to the foregoing, other system aspects are described in the claims, drawings, and text forming a part of the present disclosure.

A computationally implemented system includes, but is not limited to: circuitry for determining an incrementally progressive series of adjustment appliances, each of the series of adjustment appliances having geometries selected to progressively reposition teeth; and circuitry for determining for each of the series of adjustment appliances, a vertical displacement and a forward mandibular position for treating sleep apnea. In addition to the foregoing, other system aspects are described in the claims, drawings, and text forming a part of the present disclosure.

A method includes determining an incrementally progressive series of adjustment appliances, each of the series of adjustment appliances having geometries selected to progressively reposition teeth; and determining for each of the series of adjustment appliances, a vertical displacement and a forward mandibular position for treating sleep apnea. In addition to the foregoing, other method aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In accordance with various embodiments, computationally implemented methods, systems, processes and articles of manufacture are provided for treating sleep apnea while straightening teeth by, inter alia, determining an incrementally progressive series of adjustment appliances, each of the series of adjustment appliances having geometries selected to progressively reposition teeth and determining for each of the series of adjustment appliances, a vertical displacement and a forward mandibular position for treating sleep apnea.

Figure 1A:
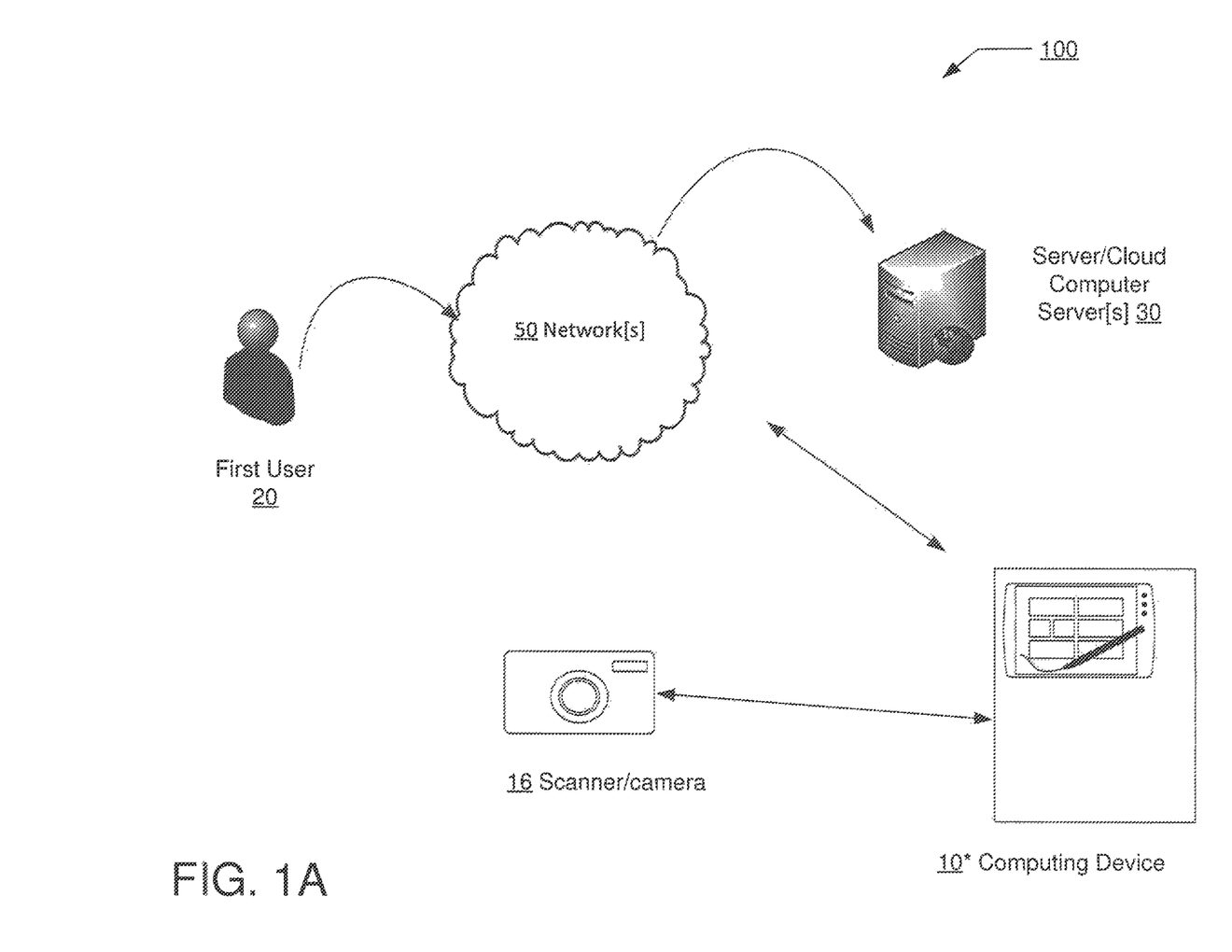
FIG. 1A shows an exemplary computing environment capable of creating a dental appliance in accordance with the present application.

Referring now to FIG. 1, the figure illustrates a computing device 10 connected via a network interface to a computer server 30 in an exemplary environment 100. As will be further described herein the illustrated computing device 10 and computer server 30 may employ the computationally implemented methods, systems, and articles of manufacture in accordance with various embodiments. The computing device 10 and computer server 30, in various embodiments, enable functions of the computing device 10.

Computing device 10 illustrated in FIG. 1 can be a tablet computer, in alternative embodiments, the computationally implemented methods, systems, and articles of manufacture in accordance with various embodiments may be embodied in other types of computer systems having other form factors including other types of portable computing devices such as, for example, mobile telephones, laptops, smartphones, e-readers, and so forth. Computing devices can include smartphones, client computers and the like as possible computing devices. As illustrated, the computing device 10 can include a display, such as a touchscreen as input/output of the computing device 10. Computing device 10 can further include a keyboard, either as a touch input/output keyboard or as an attached keyboard. As further depicted, the computing device 10 may also be connected to a scanner 16. In one embodiment, scanner 16 can be a scanning camera capable of creating a 3D image of teeth.

Figure 1B:
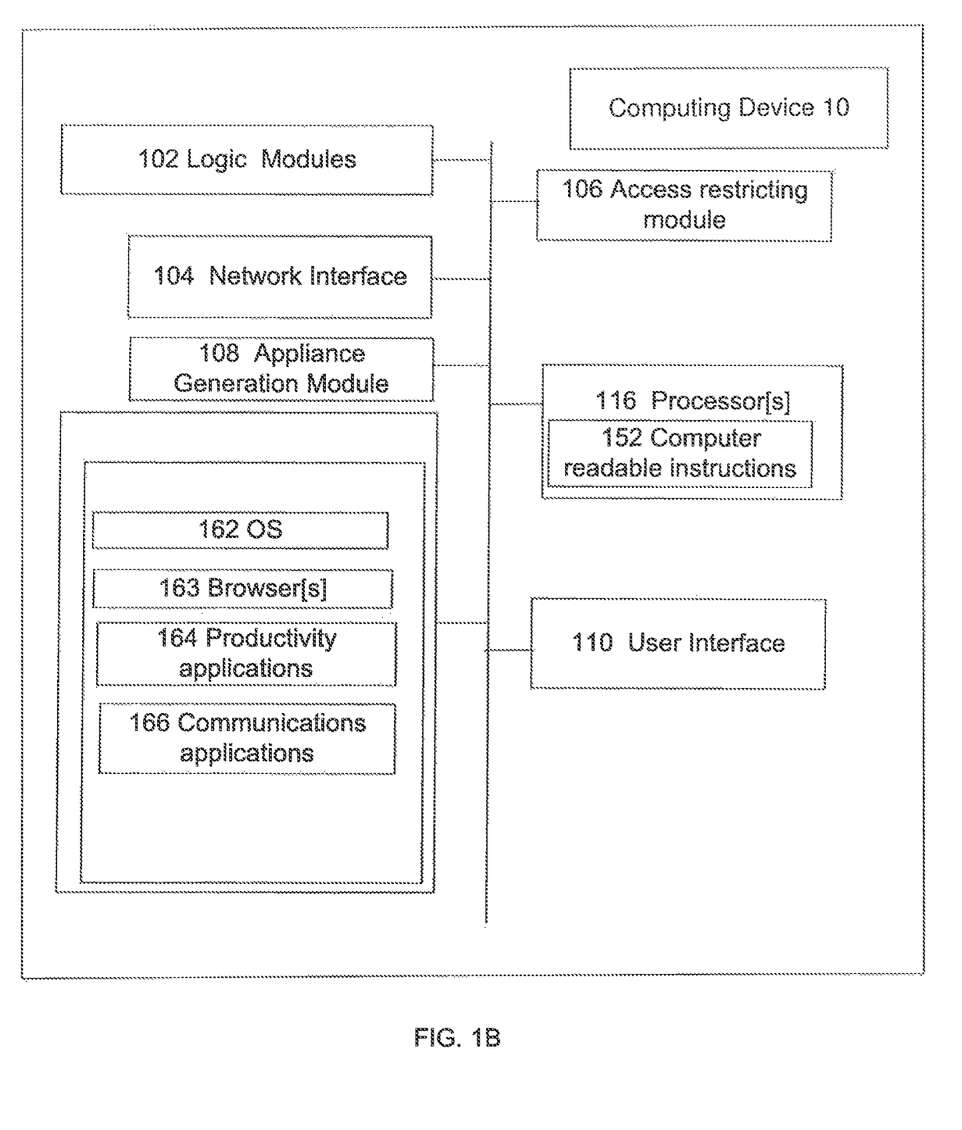
FIG. 1B illustrates an embodiment of computing device 10 shown in FIG. 1A.

Referring now to FIG. 1A, Computing device 10 is further illustrated with logic modules 102, network interface 104, user interface 110, processors 116 and memory 114. Logic modules 102 can be implemented using circuit components such as ASIC, logic modules 102 and other modules shown, may be implemented using a combination of specifically designed circuitry such as ASIC and one or more processors 116 (or other types of circuitry such as field programmable gate arrays or FPGAs) executing computer readable instructions 152. For example, in some embodiments, at least one of the logic modules may be implemented using specially designed circuitry (e.g., ASIC) while a second logic module may be implemented using a processor 116 (or other types of programmable circuitry such as an FPGA) executing computer readable instructions 152. (e.g., software and/or firmware). System requirements could dictate a combination of software and firmware and circuitry to meet the embodiments herein, for example, logic modules could be designed to use the most efficient combination of software/hardware/firmware in order to quickly implement methods and systems within the scope of the present disclosure.

In various embodiments, the memory 114 of the computing device 10 may comprise of one or more of mass storage device, read-only memory (ROM), programmable read-only memory (PROM), erasable programmable read-only memory (EPROM), cache memory such as random access memory (RAM), flash memory, synchronous random access memory (SRAM), dynamic random access memory (DRAM), and/or other types of memory devices. In various embodiments, the one or more applications 160 stored in memory 114 may include, for example, an operating system 162, a browser(s) 163, and one or more productivity applications 164 such as a word processing application or an imaging application, scanning application and one or more communication applications 166.

Computing device 10 may also include access restricting module 106. Access restricting module 106 of the computing device 10 can be configured to restrict access via the computing device 10 or preventing one or more actions by computing device 10. Computing device 10 may also include appliance generation module 108 coupled to access restricting module 106 via a bus.

Figure 2:
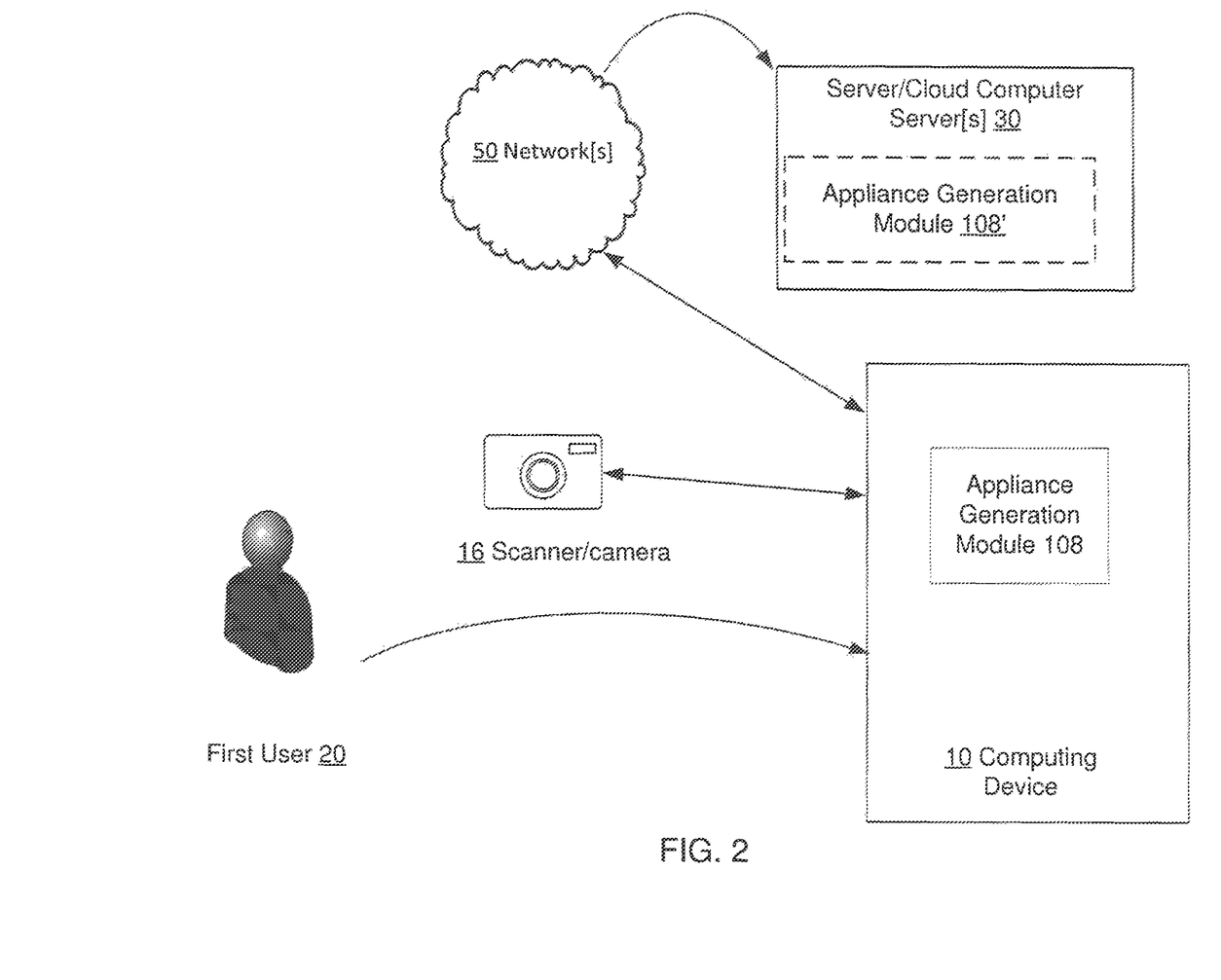
FIG. 2 shows another exemplary computing environment capable of creating a dental appliance in accordance with the present application.

Referring to FIG. 2, appliance generation module 108 may be configured to determine that a first user 20 is an authorized user attempting to operate computing device 10. Appliance generation module 108 can also be configured to determine an established authorized user based on network received data while computing device 10 is connected to a network connection. In the case of appliance generation module 108' existing in a cloud computing setting or computer server 30, appliance generation module 108 may be configured to determine a network-based authorization for the first user when first logging into network 50 or cloud computing logging to computer server 30.

In one embodiment, an appliance can be partially constructed before first user 20 handles computing device 10. In some embodiments, a manufacturer can enter data for an appliance perform authentication based on information received by first user 20 when ordering an appliance via computing device 10. In a computer server 30 environment, appliance data can be transferred from another device, via network 50 or directly by first user 20.

Appliance veneration module 108 can receive data related to various types of tooth anomalies, actions and inputs. For example, an initial appliance generated by appliance generation module 108 could be configured to adjust teeth incrementally based on predetermined inputs to computing device 10 and/or computer server 30 and/or user 20 and/or scanner/camera 16.

Incremental adjustment inputs that may be tracked for purposes of determining future appliance adjustments may be, individually or in combination, tracked using one or more sensors that may be included with the computing device 10.

Figure 3:
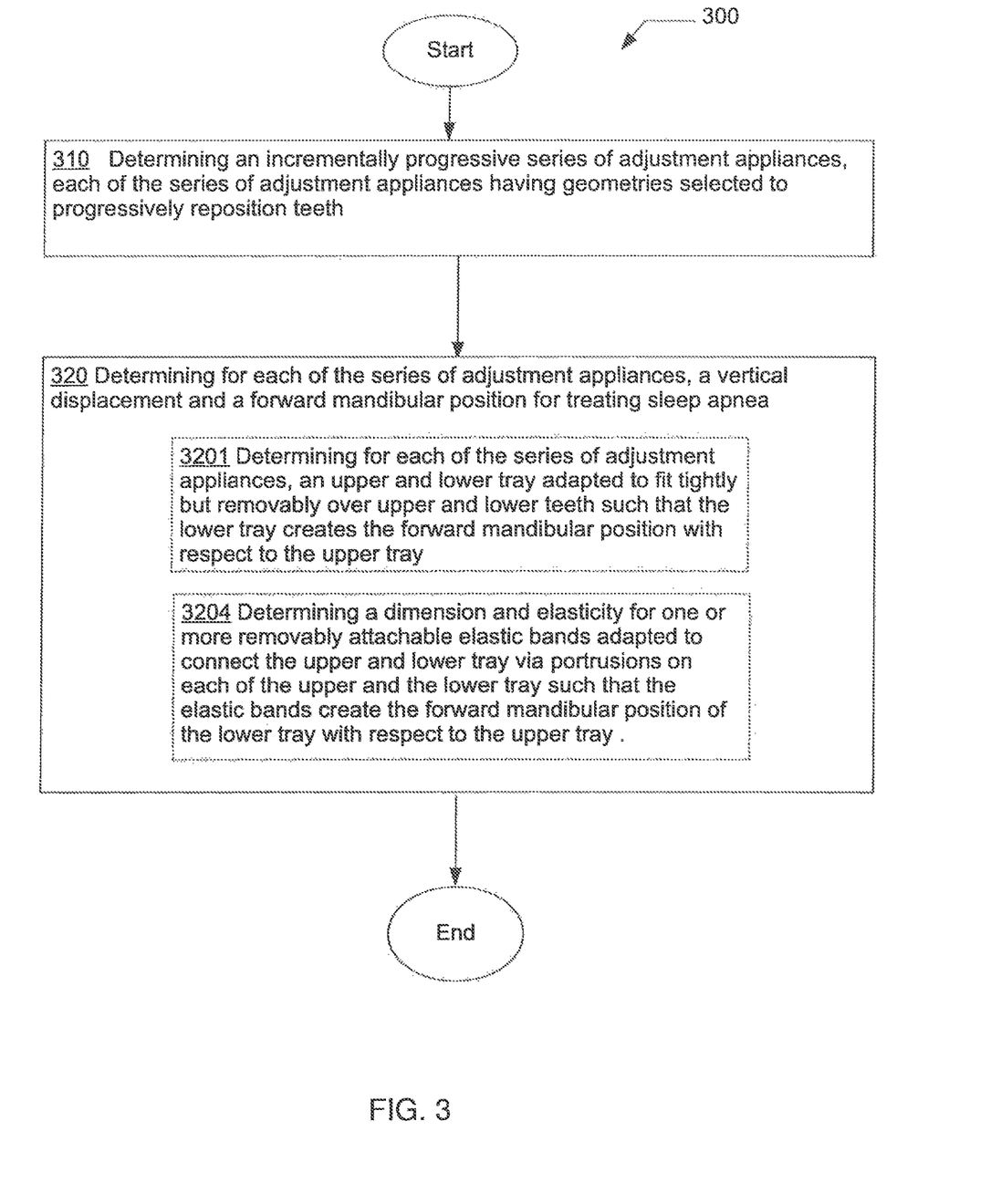
FIG. 3 is a high-level logic flowchart of a process in accordance with an embodiment of the present application.
Figure 4A:
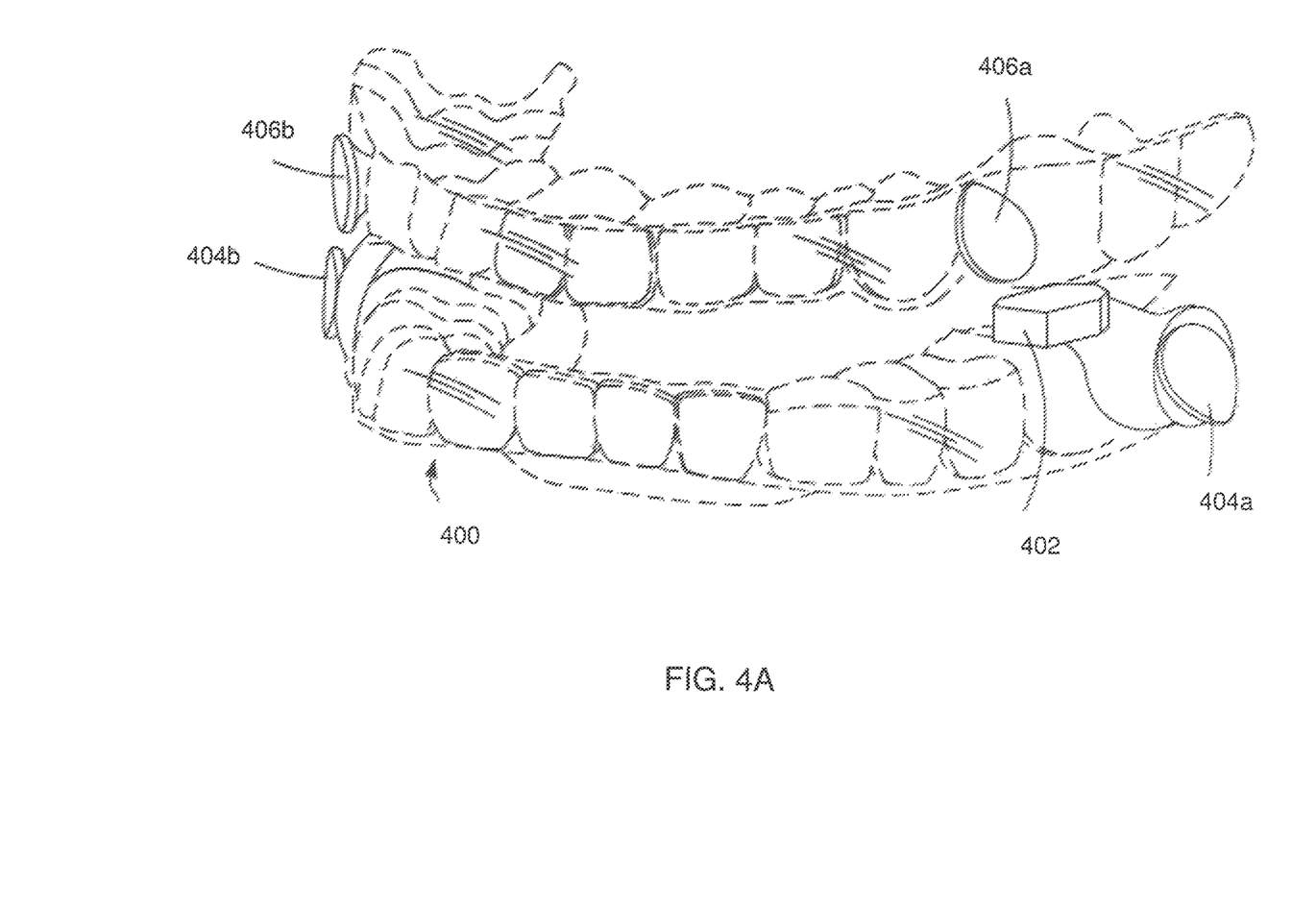
FIG. 4A is an isometric view of an upper and lower tray showing protrusions and lower bite pads in accordance with an embodiment of the present application.
Figure 4B:
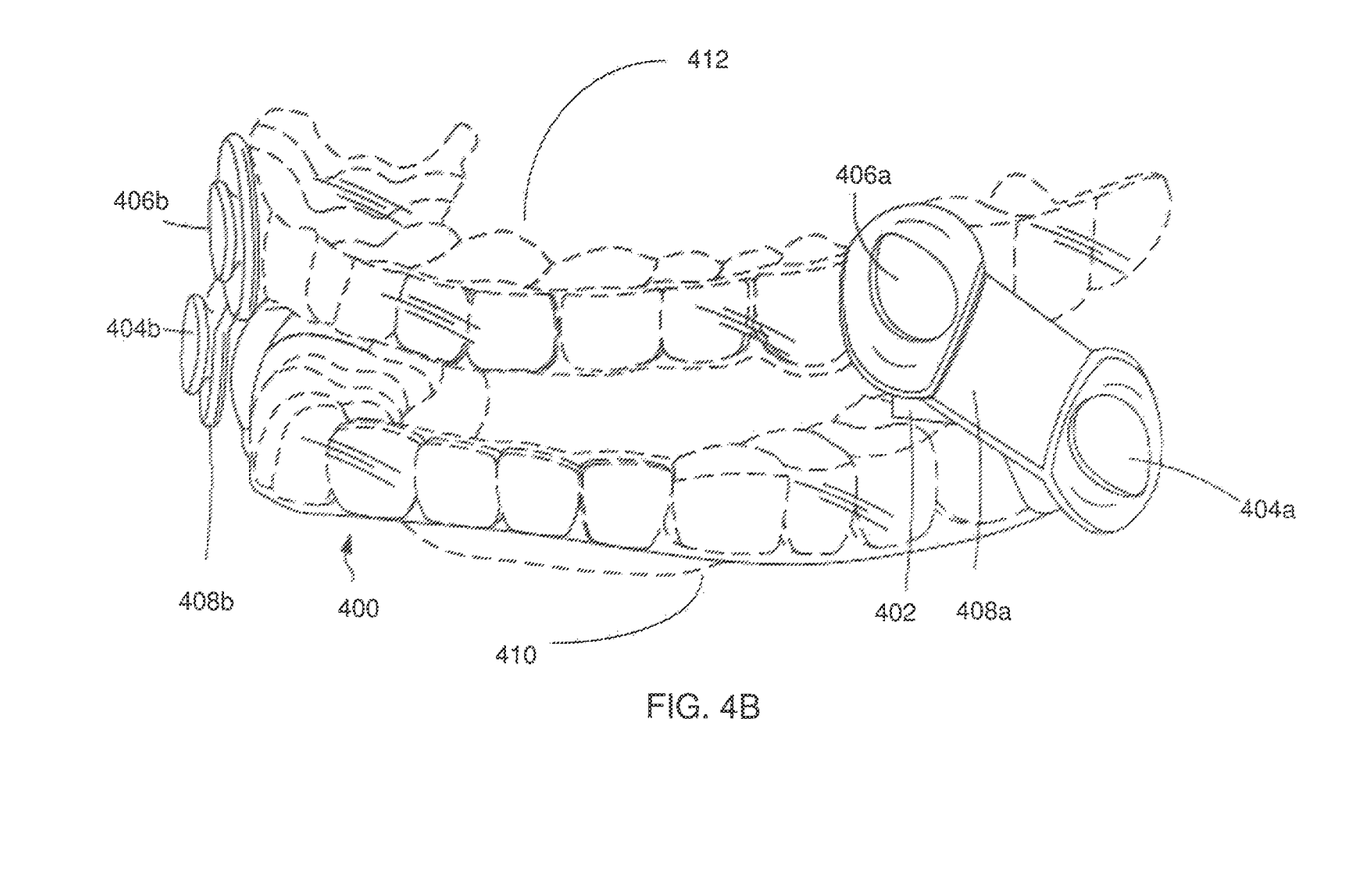
FIG. 4B is the isometric view of the upper and lower tray of FIG. 4A showing the protrusions connected by elastic bands in accordance with an embodiment of the present application.

Referring to FIG. 1 in combination with FIG. 3 and FIGS. 4A and 4B, a method for treating sleep apnea while straightening teeth includes the operational flow 300 of FIG. 3 and includes an operation 310 for determining an incrementally progressive series of adjustment appliances, each of the series of adjustment appliances having geometries selected to progressively reposition teeth. For instance, and as an illustration, a computer server 30 connecting via network 50 to the computing device 10 of FIG. 1 can establish and/or determine an incrementally progressive series of adjustment appliances associated with a patient. Operation 320 provides for determining for each of the series of adjustment appliances, a vertical displacement and a forward mandibular position for treating sleep apnea. For example, scanner 16 or molds of a patient's teeth can be examined and used to determine the adjustment needed for treating sleep apnea. Likewise, the molds or scans of a patient's teeth can be used to determine the geometries for adjusting malocclusions. FIG. 4A illustrates upper and lower trays 400 that can be created from molds. For instance, a patient with malocclusion and sleep apnea will require a determination via scanner 16 or other method. Each patient, depending on the results of scanned teeth and patient feedback, may require a different incremental displacement and a different placement of horizontal and vertical displacement for both treating sleep apnea and straightening teeth. As shown in FIG. 4A, vertical displacement can be by way of lower bite pads 402.

Operation 320 provides that the determining for each of the series of adjustment appliances, a vertical displacement and a forward mandibular position for treating sleep can include operation 3201, determining for each of the series of adjustment appliances, an upper and lower tray 400 adapted to fit tightly but removably over upper and lower teeth such that the lower tray creates the forward mandibular position with respect to the upper tray; and operation 3202 releasably attaching the forward and the rearward portions of the opposite sides of the upper and lower trays, respectively, to enable the forward mandibular position of the lower tray with respect to the upper tray. As shown in FIG. 4A, protrusions 404a and 404b on the lower tray and 406a and 406b on the upper tray are arranged to enable elastic bands to attach thereto. Referring to FIG. 4B, the elastic bands 408a and 408b are shown engaged to the upper and lower trays 400 via the protrusions. As shown in FIG. 4A, the protrusions are coupled to a vertical displacement bite pad 402.

Operation 3204 provides that the determining for each of the series of adjustment appliances, a vertical displacement and a forward mandibular position for treating sleep apnea can also include determining a dimension and elasticity for one or more removably attachable elastic bands 408*a* and 408*b* adapted to connect the upper and lower tray via protrusions' 404*a*, 404*b*, 406*a* and 406*b* on each of the upper and the lower trays 400 such that the elastic bands 404*a*, 404*b*, 406*a* and 406*b* create the forward mandibular position of the lower tray 410 with respect to the upper tray 412.

Operation 3204 includes optional operation 32042 which provides that the elastic bands can include a plurality of pairs of elastic bands, each pair being of different length and/or elasticity.

In one embodiment, the series of adjustment appliances includes an alternate series of adjustment appliances configured to be worn during sleep. More specifically, a series of adjustment appliances without the protrusions 404*a*, 404*b*, 406*a* and 406*b* and with or without vertical displacement bite pads 402 can be worn when a patient is not sleeping. That is the determining an incrementally progressive series of adjustment appliances, each of the series of adjustment appliances having geometries selected to progressively reposition teeth can continue to progressively reposition teeth when a patient is not sleeping and requiring sleep apnea treatment. The series of adjustment appliances can include upper and lower trays that are manufactured using 3D technologies such as 3D printing to enable the series of adjustment appliances to be identical with respect to the sleep apnea-enabled adjustment appliances and the non-sleep apnea-enabled adjustment appliances. In other embodiments, the series of adjustment appliances can be thermoformed using molds of a patients teeth created for the purpose of treating malocclusions and to straighten teeth.

During treatment of a patient, the series of adjustment appliances can be altered as needed. More particularly, it has been discovered that the treatment of sleep apnea can change as malocclusions, bite problems and other dental issues are resolved. For example, the size of a vertical bite pad or the strength of an elastic band may need to be altered as teeth become straightened. For this reason, in one embodiment, the initial appliance generated by appliance generation module 108 could be configured to receive later data from scanner/camera 16 to readjust teeth incrementally based on predetermined inputs to computing device 10 and/or computer server 30 and/or user 20 and/or scanner/camera 16. Using the later data, the series of adjustment appliances can be regenerated based on patient needs.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A dental appliance system, comprising:
    means for determining an incrementally progressive series of adjustment appliances, each of the series of adjustment appliances having geometries selected to progressively reposition teeth; and
    means for determining for each of the series of adjustment appliances, a vertical displacement and a forward mandibular position for treating sleep apnea.

2. The dental appliance system of claim 1, wherein the means for determining for each of the series of adjustment appliances, a vertical displacement and a forward mandibular position for treating sleep apnea includes:

means for determining an alternate series of adjustment appliances configured to be worn during sleep.

3. The dental appliance system of claim 2 wherein the incrementally progressive series of adjustment appliances are formed via a three-dimensional printing apparatus.

4. The dental appliance system of claim 1, wherein the means for determining for each of the series of adjustment appliances, a vertical displacement and a forward mandibular position for treating sleep apnea further comprises:
  means for determining for each of the series of adjustment appliances, an upper and lower tray adapted to fit tightly but removably over upper and lower teeth such that the lower tray creates the forward mandibular position with respect to the upper tray.

5. The dental appliance system of claim 4, wherein the means for determining for each of the series of adjustment appliances, an upper and lower tray adapted to fit tightly but removably over upper and lower teeth such that the lower tray creates the forward mandibular position with respect to the upper tray further comprises:
  means for releasably attaching forward and rearward portions of opposite sides of the upper and lower trays, respectively, to enable the forward mandibular position of the lower tray with respect to the upper tray.

6. The dental appliance system of claim 4, wherein the means for determining for each of the series of adjustment appliances, an upper and lower tray adapted to fit tightly but removably over upper and lower teeth such that the lower tray creates the forward mandibular position with respect to the upper tray further comprises:
  means for determining one or more removably attachable elastic bands adapted to connect the upper and lower tray via protrusions on each of the upper and the lower tray such that the elastic bands create the forward mandibular position with respect to the upper tray.

7. A computationally-implemented system, comprising:
  circuitry for determining an incrementally progressive series of adjustment appliances, each of the series of adjustment appliances having geometries selected to progressively reposition teeth; and
  circuitry for determining for each of the series of adjustment appliances, a vertical displacement and a forward mandibular position for treating sleep apnea.

8. The computationally-implemented system of claim 7, further comprising: circuitry for forming each of the series of adjustment appliances via a three dimensional printing apparatus.

9. The computationally-implemented system of claim 7, further comprising: circuitry for determining the vertical displacement appropriate for each of the series of adjustment appliances.

10. The computationally-implemented system of claim 7, further comprising: circuitry for determining one or more alternative vertical displacements appropriate for each of the series of adjustment appliances.

11. The computationally-implemented system of claim 7, further comprising: circuitry for communicating the determined incrementally progressive series of adjustment appliances and the determined vertical displacement to a three-dimensional printing apparatus.

12. The computationally-implemented system of claim 7, further comprising: circuitry for determining an alternate series of adjustment appliances configured to be worn during sleep.

13. The computationally-implemented system of claim 7, wherein the circuitry for determining for each of the series of adjustment appliances, a vertical displacement and a forward mandibular position for treating sleep apnea comprises:
  circuitry for determining for each of the series of adjustment appliances, an upper and lower tray adapted to fit tightly but removably over upper and lower teeth such that the lower tray creates the forward mandibular position with respect to the upper tray; and
  circuitry for releasably attaching forward and rearward portions of opposite sides of the upper and lower trays, respectively, to enable the forward mandibular position of the lower tray with respect to the upper tray.

14. The computationally-implemented system of claim 7, wherein the circuitry for determining for each of the series of adjustment appliances, a vertical displacement and a forward mandibular position for treating sleep apnea comprises:
  circuitry for determining a dimension and elasticity for one or more removably attachable elastic bands adapted to connect the upper and lower tray via protrusions on each of the upper and the lower tray such that the elastic bands create the forward mandibular position with respect to the upper tray.

15. The computationally-implemented system of claim 14, wherein the circuitry for determining one or more removably attachable elastic bands adapted to connect the upper and lower tray via protrusions on each of the upper and the lower tray such that the elastic bands create the forward mandibular position with respect to the upper tray comprises:
  circuitry for determining a plurality of pairs of elastic bands, each pair being of different length and/or elasticity.

16. A method for treating sleep apnea while straightening teeth, the method comprising:
  determining an incrementally progressive series of adjustment appliances, each of the series of adjustment appliances having geometries selected to progressively reposition teeth; and
  determining for each of the series of adjustment appliances, a vertical displacement and a forward mandibular position for treating sleep apnea.

17. The method of claim 16, wherein the determining an incrementally progressive series of adjustment appliances, each of the series of adjustment appliances having geometries selected to progressively reposition teeth comprises:
  receiving data pertaining to a patient;
  determining a treatment plan for progressively repositioning teeth based on the data from the patient; and
  forming the series of adjustment appliances via one or more of a three-dimensional printing apparatus or a plurality of thermoform molds.

18. The method of claim 16, wherein the determining for each of the series of adjustment appliances, a vertical displacement and a forward mandibular position for treating sleep apnea comprises:
  determining for each of the series of adjustment appliances, an upper and lower tray adapted to fit tightly but removably over upper and lower teeth such that the lower tray creates the forward mandibular position with respect to the upper tray; and
  releasably attaching forward and rearward portions of opposite sides of the upper and lower trays, respectively, to enable the forward mandibular position of the lower tray with respect to the upper tray.

19. The method of claim 16, wherein the determining for each of the series of adjustment appliances, a vertical displacement and a forward mandibular position for treating sleep apnea comprises:
- determining a dimension and elasticity for one or more removably attachable elastic bands adapted to connect the upper and lower tray via protrusions on each of the upper and the lower tray such that the elastic bands create the forward mandibular position with respect to the upper tray.

20. The method of claim 19, wherein the determining one or more removably attachable elastic bands adapted to connect the upper and lower tray via protrusions on each of the upper and the lower tray such that the elastic bands create the forward mandibular position with respect to the upper tray comprises:
- one or more instructions for determining a plurality of pairs of elastic bands, each pair being of different length and/or elasticity.

* * * * *